US010869604B2

(12) United States Patent
He (10) Patent No.: US 10,869,604 B2
(45) Date of Patent: Dec. 22, 2020

(54) ILLUMINATION DEVICE INCLUDING AN ILLUMINATOR AND A DETECTOR FOR DETECTING VITAL SIGNS OF AN OBJECT, AND USING METHOD THEREOF (71) Applicants: Hefei BOE Optoelectronics Technology Co., Ltd., Anhui (CN); BOE Technology Group Co., Ltd., Beijing (CN)

(72) Inventor: Panpan He, Beijing (CN)

(73) Assignees: Hefei BOE Optoelectronics Technology Co., Ltd., Hefei (CN); BOE Technology Group Co., Ltd., Beijing (CN)

(*) Notice: Subject to any disclaimer, the term of this patent is extended or adjusted under 35 U.S.C. 154(b) by 0 days.

(21) Appl. No.: 16/599,784

(22) Filed: Oct. 11, 2019

(65) Prior Publication Data
US 2020/0129070 A1  Apr. 30, 2020

(30) Foreign Application Priority Data

Oct. 31, 2018 (CN) .................. 2018 2 1784783 U (51) Int. Cl.
*A61B 5/00* (2006.01)
*G01N 21/01* (2006.01)
*G01D 11/28* (2006.01)
*F21V 33/00* (2006.01)
*A61N 5/06* (2006.01)
*H01H 13/02* (2006.01)

(52) U.S. Cl.
CPC ........ *A61B 5/0082* (2013.01); *F21V 33/0064* (2013.01); *F21V 33/0068* (2013.01); *G01D 11/28* (2013.01); *G01N 21/01* (2013.01); *H01H 13/023* (2013.01); *A61N 2005/0661* (2013.01); *G01N 2201/0221* (2013.01)

(58) Field of Classification Search
CPC ......... G01D 11/28; A61B 1/06; A61B 1/0638; A61B 1/0661; F21V 33/0064; F21V 33/0068; F21V 33/008
See application file for complete search history.

(56) References Cited

U.S. PATENT DOCUMENTS

| 10,311,352 | B2 * | 6/2019 | Cannell | G16H 40/40 |
| 2012/0329292 | A1 * | 12/2012 | Fish | A61B 5/002 439/39 |
| 2016/0136312 | A1 * | 5/2016 | Park | F21V 33/0044 362/231 |

(Continued)

FOREIGN PATENT DOCUMENTS

CN 105640714 A 6/2016
CN 207298719 U 5/2018

OTHER PUBLICATIONS

Machine translation of Qin, CN 105640714 A, published Jun. 8, 2016 (Year: 2016).*

(Continued)

*Primary Examiner* — William N Harris
(74) *Attorney, Agent, or Firm* — Banner & Witcoff, Ltd.

(57) ABSTRACT

An illumination device and a using method of the illumination device are provided. The illumination device includes a housing, an illuminator fixed to the housing and a detector installed on the housing, and the detector is configured to detect vital signs of an object to be detected.

18 Claims, 5 Drawing Sheets

(56) References Cited

U.S. PATENT DOCUMENTS

| | | | |
|---|---|---|---|
| 2018/0293478 A1* | 10/2018 | Cannell | G06K 19/0723 |
| 2019/0145473 A1* | 5/2019 | Puterbaugh | F16M 11/2064 |
| | | | 188/218 R |
| 2020/0029837 A1* | 1/2020 | Joudi | A61B 5/0006 |

OTHER PUBLICATIONS

May 31, 2019—(CN) First Office Action Appn 201821784783.7 with English Translation.

* cited by examiner

ILLUMINATION DEVICE INCLUDING AN ILLUMINATOR AND A DETECTOR FOR DETECTING VITAL SIGNS OF AN OBJECT, AND USING METHOD THEREOF

CROSS REFERENCE TO RELATED APPLICATIONS

The present application claims priority of Chinese Patent Application No. 201821784783.7 filed on Oct. 31, 2018, the disclosure of which is incorporated herein by reference in its entirety as part of the present application.

TECHNICAL FIELD

At least one embodiment of the present disclosure relates to an illumination device and a using method of the illumination device.

BACKGROUND

In recent years, with the improvement of living standards, people's requirements for medical services are also getting higher and higher. However, medical personnel may encounter insufficient illumination in outdoor emergency, so it is necessary to provide a portable illumination device for treating patients. However, a current illumination device may only be used for illumination, with limited functions, and inconvenient to use.

SUMMARY

At least one embodiment of the present disclosure provides an illumination device, the illumination device comprises a housing, an illuminator fixed to the housing and a detector installed on the housing, and the detector is configured to detect vital signs of an object to be detected.

For example, in the illumination device provided by at least one embodiment of the present disclosure, the detector comprises a heart rate sensor, a sphygmomanometer, a temperature sensor or an oximeter, and the detector is magnetically attached to the housing.

For example, in the illumination device provided by at least one embodiment of the present disclosure, the housing comprises a first bracket, a magnet is provided in the first bracket, the detector comprises a casing, and the casing comprises a magnetic adsorption material.

For example, in the illumination device provided by at least one embodiment of the present disclosure, the illuminator comprises an illumination lamp and a sterilizing lamp.

For example, in the illumination device provided by at least one embodiment of the present disclosure, the illuminator further comprises a light converging plate configured to converge light emitted from the illumination lamp and the sterilizing lamp.

For example, the illumination device provided by at least one embodiment of the present disclosure further comprises a control device fixed to the housing, the control device is connected to the detector in a signal connection manner to receive detection information from the detector.

For example, in the illumination device provided by at least one embodiment of the present disclosure, the control device comprises a control chip and a control switch, the control chip is in the housing, and the control switch is configured to control power-on and power-off of the control chip.

For example, the illumination device provided by at least one embodiment of the present disclosure further comprises a display screen, the display screen is fixed to the housing and connected to the control device in a signal connection manner.

For example, the illumination device provided by at least one embodiment of the present disclosure further comprises a first lifting mechanism and a first driving element, the first lifting mechanism is configured to fix the illuminator to the housing, a first driving element is connected to the control device in a signal connection manner and configured to receive a control signal from the control device to drive the first lifting mechanism to move telescopically for moving the illuminator in a direction away from or close to the housing.

For example, the illumination device provided by at least one embodiment of the present disclosure further comprises a second driving element, the second driving element is connected to the control device in a signal connection manner and configured to drive the illuminator to rotate for adjusting a light emitting angle.

For example, in the illumination device provided by at least one embodiment of the present disclosure, the housing comprises a storage tank, and a shape of the storage tank is matched with an outer shape of the illuminator so that the illuminator is accommodated in the storage tank after being retrieved.

For example, the illumination device provided by at least one embodiment of the present disclosure further comprises a support part, the support part is connected to the housing for supporting the illumination device.

For example, in the illumination device provided by at least one embodiment of the present disclosure, the support part comprises at least one second lifting mechanism and at least one third driving element, one end of the second lifting mechanism is connected to the housing and an other end of the second lifting mechanism is movable, and the at least one third driving element is connected to the control device in a signal connection manner and configured to drive the second lifting mechanism to extend or contract so that the other end of the second lifting mechanism moves in a direction away from or close to the housing, thereby adjusting a level degree of the housing.

For example, in the illumination device provided by at least one embodiment of the present disclosure, the support part comprises a plurality of second lifting mechanisms, each of the plurality of second lifting mechanism is correspondingly connected to one third driving element, and the plurality of second lifting mechanisms are respectively adjusted for adjusting the level degree of the housing, so that the illumination device is stably supported.

For example, in the illumination device provided by at least one embodiment of the present disclosure, the support part comprises a plurality of second lifting mechanisms, at least two of the plurality of second lifting mechanism are correspondingly connected to one third driving element, and the plurality of second lifting mechanisms are respectively adjusted for adjusting the level degree of the housing, so that the illumination device is stably supported.

For example, the illumination device provided by at least one embodiment of the present disclosure further comprises a level sensor, the level sensor is mounted to the housing and configured to detect the level degree of the housing and transmit the detected level degree to the control device, the control device adjusts the plurality of second lifting mechanisms according to the detected level degree.

For example, in the illumination device provided by at least one embodiment of the present disclosure, the illumination device is a portable illumination device, and the illumination device further comprises a portable belt provided on an upper side of the housing.

For example, in the illumination device provided by at least one embodiment of the present disclosure, the control device comprises an audio control chip and a sound signal processing chip, the audio control chip is connected to the control chip in a signal connection manner and configured to receive a control instruction from the control chip, the sound signal processing chip is connected to the control chip in a signal connection manner and configured to receive a sound signal and convert the sound signal into a control signal, and transmit the control signal to the control chip; the illumination device further comprises a speaker and a microphone, the speaker is arranged on the housing and connected in a signal connection manner to the audio control chip and plays a fixed audio signal or an audio signal provided by the audio control chip according to a control of the audio control chip, and the microphone is arranged on the housing and configured to receive a sound input from a user and transmit the sound input to the sound signal processing chip.

At least one embodiment of the present disclosure provides a using method of the illumination device as mentioned above, the using method comprises: in a case where the detector is used to detect the vital signs of the object to be detected and illumination is required, turning on the illuminator for illumination.

For example, the using method provided by at least one embodiment of the present disclosure further comprises: controlling the at least one third driving element by using the control device to drive the at least one second lifting mechanism to extend or contract, to adjust the level degree of the housing, so that the illumination device is stably supported.

For example, the using method provided by at least one embodiment of the present disclosure further comprises: detecting the level degree of the housing by adopting the level sensor and transmitting the level degree to the control device; and determining whether the housing is level according to the level degree detected by the level sensor, and controlling the at least one second lifting mechanism to extend or contract for improving the level degree of the housing in a case where the illumination device is not stably supported.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

FIG. 2 is a specific structural schematic diagram of the illumination device illustrated in

FIG. 1;

REFERENCE NUMERAL

1—housing; 2—portable belt; 3—control device; 4—control box; 5—circuit board; 6—control switch; 7—control chip; 8—display screen; 9—display driving chip; 10—speaker; 11—audio control chip; 12—microphone; 13—sound signal processing chip; 14—illuminator; 15—illumination bracket; 16—lamp bracket; 17—light converging plate; 18—illumination lamp; 19—illuminator driving chip; 20—sterilizing lamp; 21—first lifting mechanism; 22—power controller; 23—first driving element; 24—first driving chip; 25—detector; 26—first bracket; 27—magnet; 28—casing; 29—connection line of detection device; 30—heart rate sensor; 31—sphygmomanometer; 32—support part; 33—second lifting mechanism; 34—support base; 35—driving motor; 36—worm gear; 37—worm; 38—level sensor; 39—second driving element; 40—storage tank.

DETAILED DESCRIPTION

In order to make objects, technical details and advantages of the embodiments of the invention apparent, the technical solutions of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

Unless otherwise defined, all the technical and scientific terms used herein have the same meanings as commonly understood by one of ordinary skill in the art to which the present disclosure belongs. The terms, such as "first," "second," or the like, which are used in the description and the claims of the present disclosure, are not intended to indicate any sequence, amount or importance, but for distinguishing various components. The terms, such as "comprise/comprising," "include/including," or the like are intended to specify that the elements or the objects stated before these terms encompass the elements or the objects and equivalents thereof listed after these terms, but not preclude other elements or objects. The terms, such as "connect/connecting/connected," "couple/coupling/coupled" or the like, are not limited to a physical connection or mechanical connection, but may include an electrical connection/coupling, directly or indirectly. The terms, "on," "under," "left," "right," or the like are only used to indicate relative position relationship, and when the position of the object which is described is changed, the relative position relationship may be changed accordingly.

At least one embodiment of the present disclosure provides an illumination device, which includes a housing, an illuminator and a detector, the illumination may be a portable illumination device. The illuminator is fixed to the housing, the detector is mounted to the housing, and the detector is configured to detect vital signs of an object to be detected. The illumination device is provided with the detector, thus the illumination device has a vital sign detection function, and users, such as medical personnel, may carry the illumination device to detect the patient condition and monitor the patient condition in real time in the process of performing emergency medical treatment, so that relevant detection equipment may be unnecessary to carry, and the application capability of the illumination device in the medical field is significantly improved.

Next, the illumination device according to at least one embodiment of the present disclosure will be described with reference to the accompanying drawings.

Figure 1:
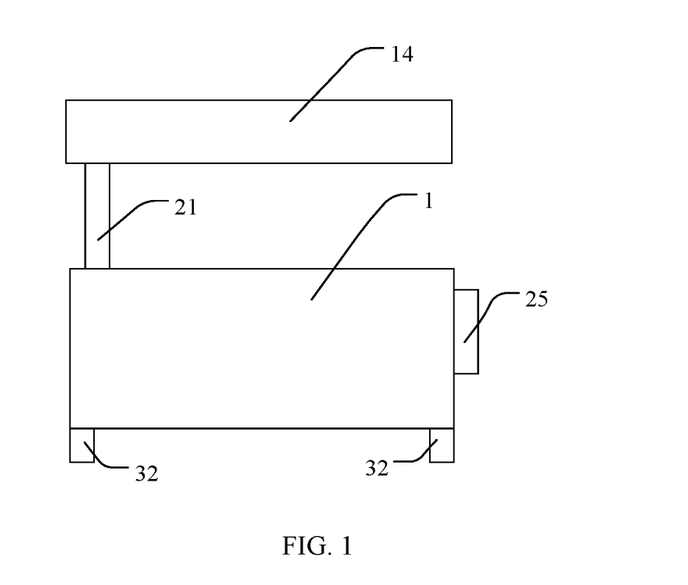
FIG. 1 is a structural schematic diagram of an illumination device provided by an embodiment of the present disclosure.

FIG. 1 is a structural schematic diagram of an illumination device provided by an embodiment of the present disclosure. As illustrated in FIG. 1, the illumination device includes a housing 1, an illuminator 14 and a detector 25. The illuminator 14 is fixed to the housing 1, and the detector 25 is mounted to the housing 1. The detector 25 is configured to detect vital signs of an object to be detected. For example, the detector 25 is detachably mounted on the housing 1. When in use, the detector 25 is detached from the housing 1 to detect a patient, and when not in use, the detector 25 is mounted to the housing 1, which is convenient to carry.

Figure 2:
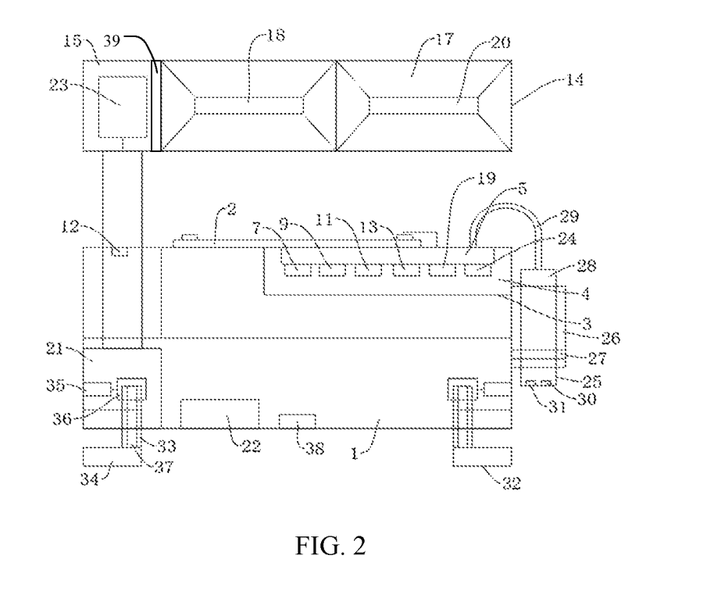
Figure 3A:
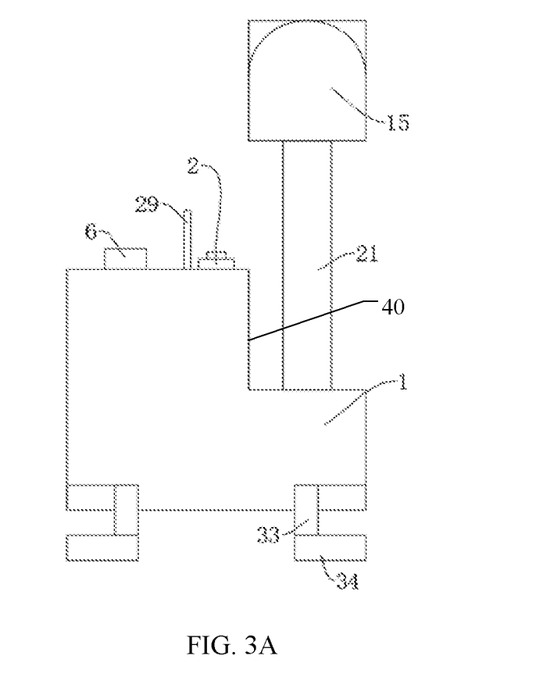
FIG. 3A is a left view of the illumination device illustrated in FIG. 2 under a first state.
Figure 3B:
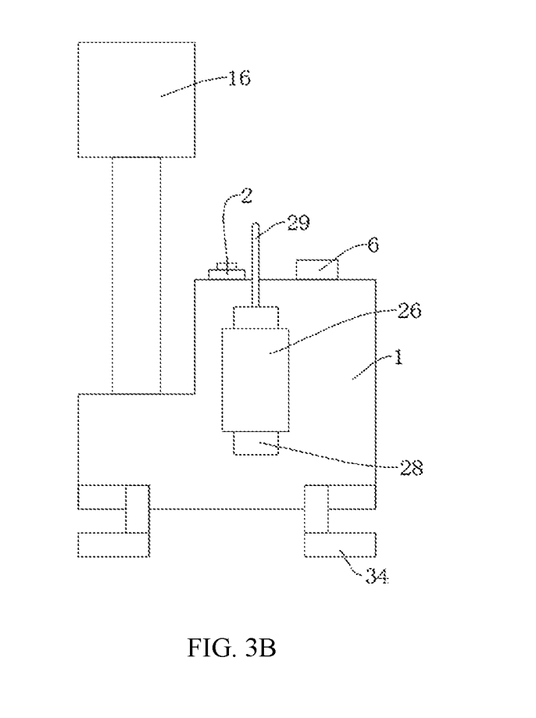
FIG. 3B is a right view of the illumination device illustrated in FIG. 2 under a first state.
Figure 3C:
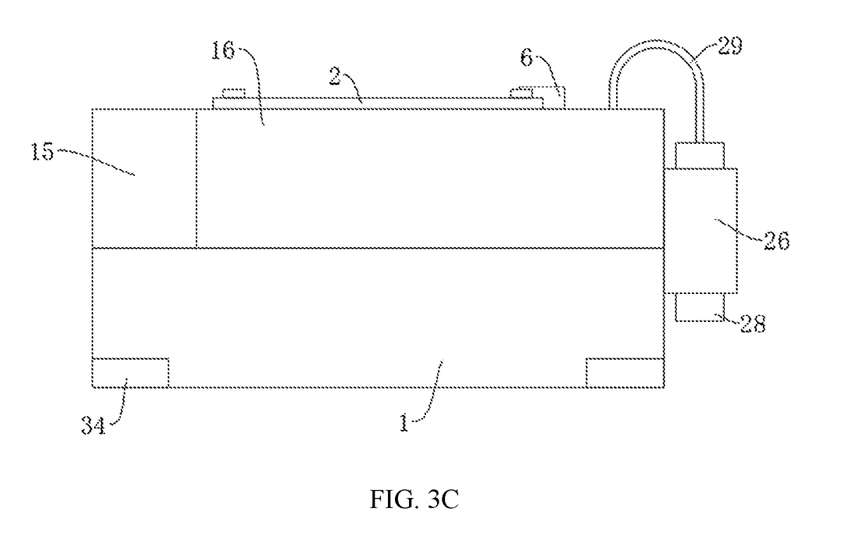
FIG. 3C is a front view of the illumination device illustrated in FIG. 2 under a second state.
Figure 3D:
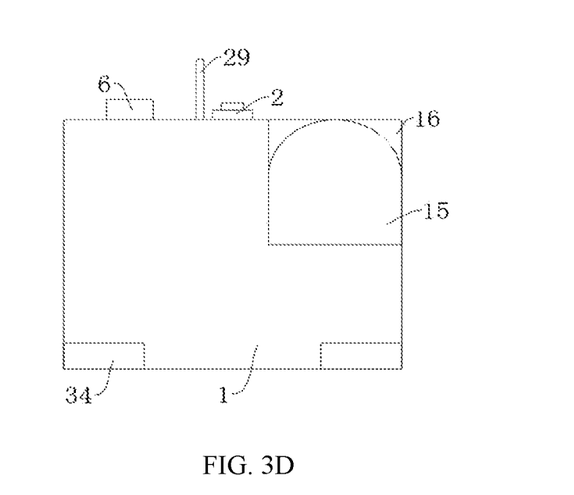
FIG. 3D is a left view of the illumination device illustrated in FIG. 2 under a second state.
Figure 3E:
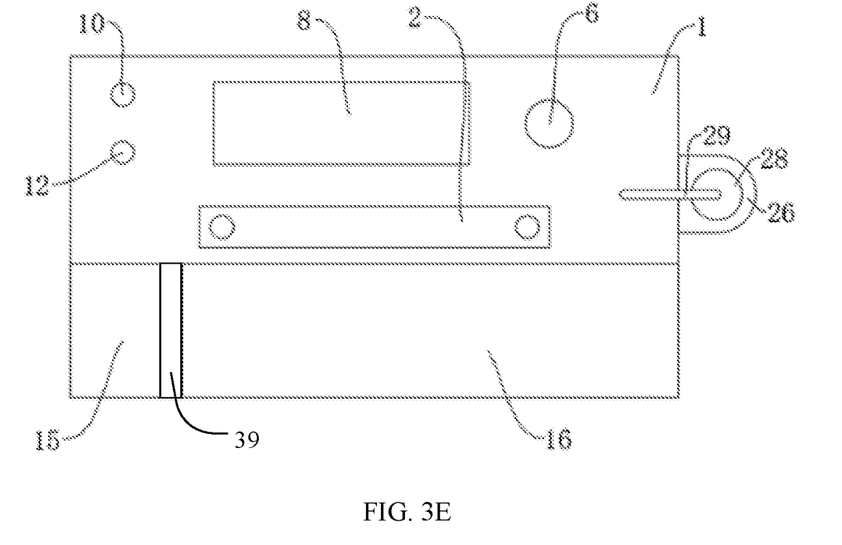
FIG. 3E is a top view of the illumination device illustrated in FIG. 2.
Figure 3F:
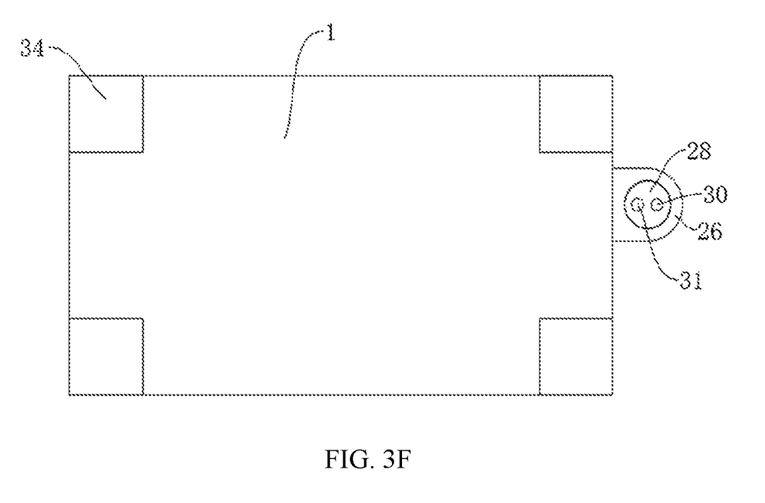
FIG. 3F is a bottom view of the illumination device illustrated in FIG. 2.
Figure 3G:
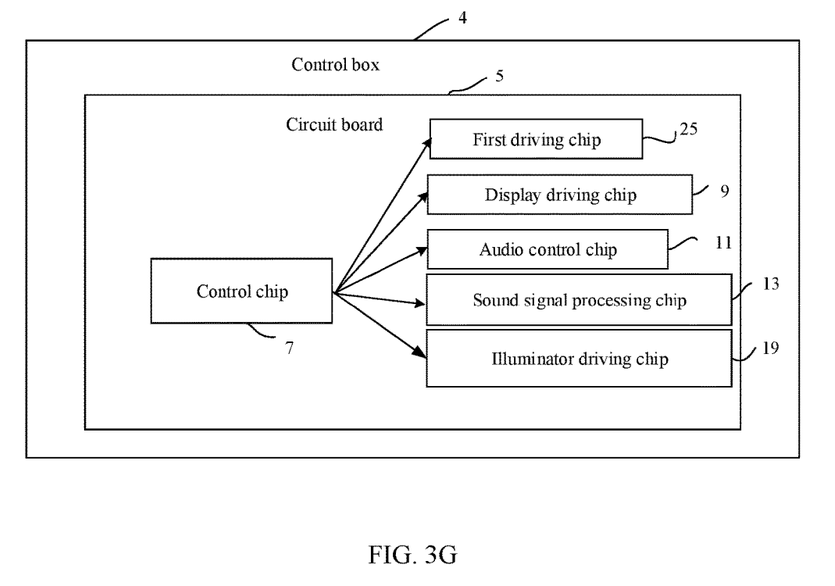
FIG. 3G is a structural block diagram of a control device of the illumination device illustrated in FIG. 2.
Figure 3H:
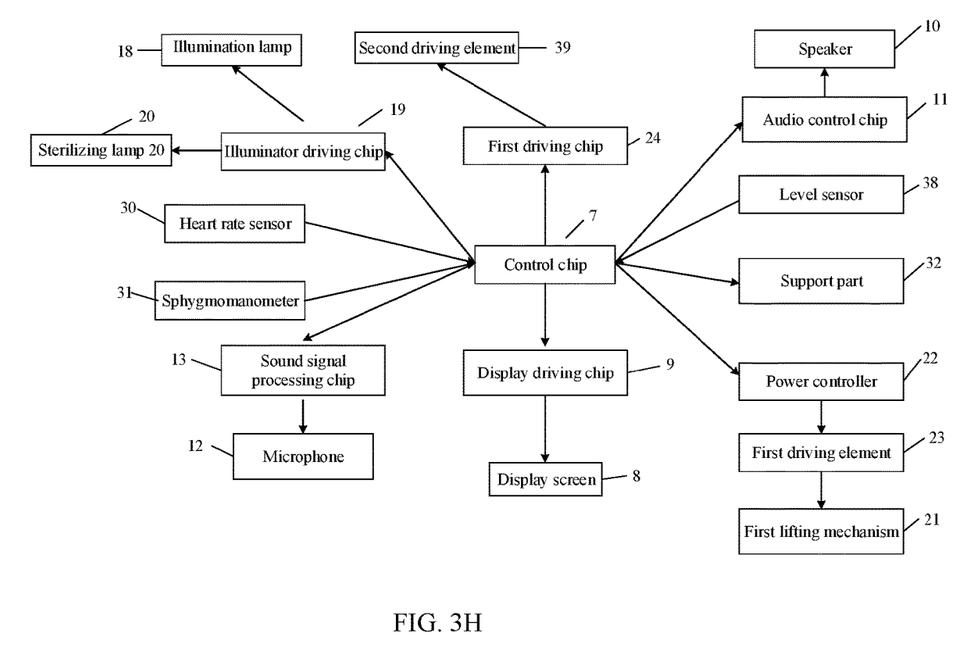
FIG. 3H is a schematic diagram of a signal transmission relationship between elements of the illumination device illustrated in FIG. 2.

FIG. 2 is an exemplary structural diagram of an illumination device provided by an embodiment of the disclosure; FIG. 3A is a left view of the illumination device illustrated in FIG. 2 under a first state; FIG. 3B is a right view of the illumination device illustrated in FIG. 2 under the first state; FIG. 3C is a front view of the illumination device illustrated in FIG. 2 under a second state; FIG. 3D is a left view of the illumination device illustrated in FIG. 2 under the second state; FIG. 3E is a top view of the illumination device illustrated in FIG. 2; FIG. 3F is a bottom view of the illumination device illustrated in FIG. 2; FIG. 3G is a structural block diagram of a control device of the illumination device illustrated in FIG. 2; and FIG. 3H is a schematic diagram of a signal transmission relationship between elements of the illumination device illustrated in FIG. 2. The first state is a state where the illuminator 14 is used, and the second state is a state where the illuminator 14 is not used and is placed in a storage tank 40 of the housing 1.

In at least one embodiment of the present disclosure, there is no limitation on the type of the detector and the type of vital signs that the detector may detect, and the vital signs may include heart rate, pulse rate, blood pressure, body temperature, blood glucose, blood oxygen saturation, respiration rate, etc. For example, in the illumination device provided by at least one embodiment of the present disclosure, the detector may include a heart rate sensor, a sphygmomanometer (non-invasive sphygmomanometer), a temperature sensor, an oximeter, and other detection devices that may detect vital signs of a user. Typically, as illustrated in FIG. 2, the detector 25 includes a heart rate sensor 30 and a sphygmomanometer 31. The sphygmomanometer 31 may be a non-invasive sphygmomanometer. For example, the heart rate sensor 30 may be a PAH8001EI-2G type heart rate sensor, and the sphygmomanometer 31 may be a 30INCH-G-BASIC type pressure sensor.

In at least one embodiment of the present disclosure, there is no limitation on the manner in which the detector is mounted on the housing. For example, in some embodiments of the present disclosure, the detector may be in snap-fit connection with the housing, or the detector may be suspended from the housing. For example, in other embodiments of the present disclosure, the detector is magnetically attached to the housing, so that the detector may be firmly installed on the housing, is not easy to fall off from the housing during shaking, and is convenient to disassemble. For example, the detector may also be arranged in the housing, a groove may be arranged in the housing, and the detector may be inserted into or pulled out of the groove. For example, the groove and the detector (e.g., the casing of the detector) may be in a snap-fit connection or a threaded connection. For example, the groove may be provided as a female snap-fit, and the detector may include a male snap-fit constituted of an elastic material or an elastic structure; alternatively, an inner wall of the groove and an outer wall (the casing) of the detector are both provided with threads matching each other, and the detector may be screwed in and out of the groove. In this way, in a case where the illumination device is carried, the housing may protect the detector, so that the detector is not exposed to an external environment, and the risk of the detector damage due to factors such as collision may be reduced.

For example, in the illumination device provided by some embodiments of the present disclosure, the housing includes a first bracket in which a magnet is provided. The detector includes a casing, and the casing includes a magnetic adsorption material. Typically, as illustrated in FIGS. 2 and 3A-3H, the housing 1 is provided with a first bracket 26, and the detector 25 under an unused state may be placed in the first bracket 26. The first bracket 26 is provided with a magnet 27, and the detector 25 includes a casing 28 which is at least partially made of a magnetic material. In this way, the detector 25 may be magnetically attached to the first bracket 26. For example, the magnetic material may be a metal such as iron, cobalt, nickel, or an alloy thereof. For example, the housing 1, the first bracket 26 and the magnet 27 are firmly connected using screws. For example, the casing 28 is firmly connected with a sensor such as a heart rate sensor 30, a sphygmomanometer 31 using screws.

For example, in the illumination device provided by other embodiments of the present disclosure, a magnet is provided in the first bracket of the housing, and the casing of the detector also includes a magnet. In this way, a magnetic attraction force between the housing and the detector is large, and the detector is not easy to fall off. For example, in the illumination device provided by other embodiments of the present disclosure, the first bracket of the housing includes a magnetic material, and the casing of the detector is provided with a magnet.

For example, in the illumination device provided by at least one embodiment of the present disclosure, an illuminator includes an illumination lamp and a sterilizing lamp. Typically, as illustrated in FIG. 2 and FIGS. 3A-3H, the illuminator 14 includes an illumination bracket 15 and a lamp bracket 16. The illumination bracket 15 is used for supporting the lamp bracket 16, and an illumination lamp 18 and a sterilizing lamp 20 are mounted in the lamp bracket 16. The control device 3 includes an illuminator drive chip 19 to control the illumination lamp 18 and the sterilizing lamp 20. The illumination lamp 18 may be an LED lamp and may be other types of illuminators. The sterilizing lamp 20 may be an ultraviolet sterilizing lamp. For example, the illumination lamp 18 may be a FR-4 type LED lamp, the sterilizing lamp 20 may be a TL-D15 W type ultraviolet sterilizing lamp, and the illuminator drive chip 19 may be a SM2202P type high-power linear constant current drive chip.

For example, in the illumination device provided by at least one embodiment of the present disclosure, the illuminator may further include a light converging plate, and the light converging plate is configured to converge light emitted from the illumination lamp and the sterilizing lamp. Typically, as illustrated in FIG. 2 and FIGS. 3A-3H, the light converging plate 17 is installed at positions of the lamp bracket 16 corresponding to the illumination lamp 18 and the sterilizing lamp 20. The light converging plate 17 may improve the illumination effect of the illumination lamp 18, and improve the disinfection effect of the sterilizing lamp 20, thereby improving the light utilization rate, and reducing power consumption.

For example, the illumination device provided by at least one embodiment of the present disclosure further includes a control device fixed to a housing, and the control device is connected to a detector in a signal connection manner to receive detection information of the detector. Typically, as illustrated in FIGS. 2 and 3A-3H, the control device 3 is installed in the housing 1. For example, the control device 3 may be connected in a signal connection manner to the detector 25 via a detection device connection line 29; alternatively, the control device may be configured to be wirelessly connected to the detector. For example, the control device may be configured to control other elements such as the illuminator 14, a display screen, a support part, an audio control element in the following embodiments, etc. For example, the control device 3 may analyze, store, feedback the information detected by the detector 25 to realize automatically detecting vital signs of a patient.

For example, in the illumination device provided by at least one embodiment of the present disclosure, the control device includes a control chip and a control switch. The control chip is located in the housing, and the control switch is configured to control the power on and off of the control chip. For example, in a case where the control switch is closed, the control chip is powered on to operate normally, and in a case where the control switch is opened, the control chip is powered off to stop operating. Typically, as illustrated in FIGS. 2 and 3G, the control device 3 includes a control box 4 installed inside the housing 1, the control box 4 includes a circuit board 5 on which a control chip 7 is installed, and a control switch 6 is installed outside the housing 1. The control switch 6 may control the on-off of the control chip 7. For example, the control switch 6 may also be used as a power switch for the entire illumination device. The control box 4 may protect the control chip 7. For example, the control chip 7 may be an IC697CPM790 type central processor chip.

For example, the control device may further include a plurality of driving chips, such as a display driving chip 9, an audio control chip 11, a sound signal processing chip 13, an illuminator driving chip 19, a first driving chip 24, and the like, to control functions of other elements in the illumination device (referring to the display screen, the support part, and the like described below). For example, the control chip 7 may be configured to control functions of the driving chip described above. For example, the control chip and the above driving chip may soldered to the circuit board 5, which is firmly connected to the control box 4 by screws.

For example, the illumination device may further include a speaker 10 and a microphone 12, the speaker 10 is provided on the housing, connected to the audio control chip in a signal connection manner, and plays a fixed audio signal or an audio signal provided by the audio control chip according to the control of the audio control chip, and the microphone 12 is provided on the housing and configured to receive a sound input from a user and transmit a sound signal to the sound signal processing chip.

For example, in a case where an emergency occurs to the detected object, for example, vital signs exceed a normal range, for example, heart rate, blood pressure, etc. exceed the normal range, the control chip of the control device connected to the detector acquires this vital sign information, and in a case where it is determined that the vital sign information exceeds the normal range, sends a control signal to the audio control chip, so that the audio control chip turns on the speaker, plays a fixed audio signal, such as an alarm sound, etc., or plays an audio signal sent by the audio control chip, such as vital sign data, etc., which is not limited by the embodiments of the present disclosure.

For example, users, such as medical personnel, may also use a microphone to input sound. The sound signal is transmitted to the sound processing chip, and the sound processing chip converts the sound signal into a control signal and transmits the control signal to the control chip. The control chip controls a corresponding operation according to the control signal. For example, the control signal may be a control signal that controls the illuminator to extend for providing illumination, or may be a control signal that controls the illuminator to rotate, etc. The embodiment of the present disclosure is not limited to this.

For example, the illumination device provided by at least one embodiment of the present disclosure further includes a display screen, which is fixed to the housing and connected to the control device in a signal connection manner. Typically, as illustrated in FIG. 2, a display screen 8 is provided outside the housing 1, and the control device 3 includes a display driving chip 9 for controlling the display screen 8. For example, the control device 3 may present the information detected by the detector 25 on the display screen 8, so that medical personnel or patients may more intuitively know the status of vital signs. For example, the control device may also present information of other elements (e.g., level degree, brightness, etc.) on the display screen. For example, the display screen 8 may be an M077C type LCD liquid crystal display screen, and the display driving chip 9 may be a ME2604 type constant current driving chip.

For example, the display screen may include a liquid crystal display panel, an OLED display panel, an electronic paper display panel, or other types of display panels. For example, the display screen may also include a touch panel to have a touch function. For example, the touch panel may be integrated in the above display panel. In this way, a user may send instructions to the control device through the display screen with a touch control function for controlling functions of elements of the illumination device.

For example, the illumination device provided by at least one embodiment of the present disclosure further includes a first lifting mechanism and a first driving element. An illuminator is fixed to a housing through the first lifting mechanism, and the first driving element is connected to a control device in a signal connection manner and is configured to drive the first lifting mechanism to move telescopically so as to move the illuminator in a direction away from or close to the housing. Typically, as illustrated in FIGS. 2 and 3A-3H, the illumination device includes a first lifting mechanism 21 and a first driving element 23. An end of the first lifting mechanism 21 is fixed to the housing 1, and the other end is connected to the illumination bracket 15, so that the illuminator 14 is fixed to the housing 1 through the first lifting mechanism 21. For example, the first lifting mechanism 21 may include an electric push rod, and the first drive element 23 may include a servo motor. For example, the servo motor may be a DS-25RS370 type deceleration motor, and the first lifting mechanism 21 may include a DE24-

17W42-02FP041 type electric push rod. For example, the first lifting mechanism 21, the first driving element 23 and the illumination bracket 15 are firmly connected using screws.

For example, the electric push rod may include an element such as a reduction gear, a screw, a nut, a guide sleeve, a push rod, a sliding base, a spring, a casing, a worm gear, a micro-motion control switch, etc. Typically, the motor (e.g., the first driving element 23) may drive a pair of screw nuts after being decelerated by the reduction gear, thereby changing a rotational motion of the motor into a linear motion, and completing a pushing rod action by using the forward rotation or reverse rotation of the motor, i.e., making the length of the push rod larger or smaller. For example, the electric push rod may in a worm and worm gear transmission manner, and may also choose gear transmission.

For example, as illustrated in FIGS. 2 and 3A-3H, the illumination device may also include a power controller 22, which is connected to the first driving element 23 for controlling the on/off of the first driving element 23. For example, the power controller 22 may be connected to the control device 3 in a signal connection manner. For example, the power controller 22 may be a WB-D-4 type power detector.

For example, as illustrated in FIGS. 2 and 3A-3H, the control device 3 of the illumination device includes a first driving chip 24, which is connected to the first driving element 23 and the power controller 22 in a signal connection manner. For example, the first driving chip 24 may be an A4960 type motor control chip.

For example, the illumination device provided by some embodiments of the present disclosure further includes a second driving element, which is connected to the control device in a signal connection manner and is configured to drive the illuminator to rotate for adjusting a light emitting angle. Typically, as illustrated in FIG. 2, a second driving element 39 is located between the illumination bracket 15 and the lamp bracket 16, and the second driving element 39 may drive the lamp bracket 16 to rotate relative to the illumination bracket 15, in cooperation with the light converging plate 17, so that a light emitting angle of the illumination lamp 18 and the sterilizing lamp 20 fixed in the lamp bracket 16 may be automatically adjusted. It should be noted that in other embodiments of the present disclosure, the illumination device may not be provided with the above-mentioned second driving element, and the lamp bracket 16 and the illumination bracket 15 may be in a rotatable connection. The light emitting angle of the illumination lamp 18 and the sterilizing lamp 20 may be manually adjusted when in use. For example, the second driving element 39 may include a rotating motor including a motor shaft, and the lamp bracket 16 is fixed to one end of the motor shaft. The rotation of the motor shaft of the rotating motor drives the lamp bracket 16 to rotate, so that the light emitting angle of the illumination lamp 18 and the sterilizing lamp 20 may be adjusted. For example, the second driving element 39 may include a rotating motor, a worm gear and a worm. The worm gear may be fixed to the lamp bracket 16 and the rotating motor drives the worm to rotate for driving the worm gear to rotate, so that the lamp bracket 16 is rotated, thereby the light emitting angle of the illumination lamp 18 and the sterilizing lamp 20 may be adjusted.

For example, in the illumination device provided by at least one embodiment of the present disclosure, the housing includes a storage tank whose shape matches a shape of the illuminator, so that the illuminator is accommodated in the storage tank after being retrieved, that is, in unused state, the illuminator is taken back and accommodated in the storage tank. Typically, as illustrated in FIG. 3A, the housing 1 is provided with a storage tank 40 which may accommodate the illuminator 14. Typically, in FIGS. 2, 3A and 3B, the first lifting mechanism 21 lifts the illuminator 14 out of the storage tank 40 for illuminating or sterilizing. In FIGS. 3C to 3F, the first lifting mechanism 21 lowers the illuminator 14 into the storage tank 40 for accommodating. After the illuminator 14 is accommodated in the storage tank 40, the overall shape of the housing 1 and the illuminator 14 of the illumination device may be approximately a regular three-dimensional shape such as a cuboid. For example, when the illuminator 14 is fully retracted into the housing 1, the two may form a device having a complete appearance shape. The housing 1 may be provided with an openable lid or cover that protects the illuminator 14, and in a case where the illuminator 14 is fully retracted, the lid or cover may be used to protect the illuminator. In this way, in a case where the illumination device is not used, the illumination device may be folded (the illuminator enters the storage tank), which is convenient to carry. For example, the storage tank for accommodating the illuminator may be located at an edge of the housing as illustrated in FIG. 3A, or may be located in the middle or at other positions of the housing.

For example, the illumination device provided by at least one embodiment of the present disclosure further includes a support part which is connected to the housing for supporting the housing. Typically, as illustrated in FIG. 2, the support part 32 is arranged at a bottom of the housing 1. The support part 32 may be configured to provide a plurality of fulcrums for the housing so that the illumination device may be placed stably.

For example, in the illumination device provided by at least one embodiment of the present disclosure, the support part includes at least one second lifting mechanism and at least one third driving element. One end of the second lifting mechanism is connected to the housing, the other end is movable, and the third driving element is connected to the control device in a signal connection manner and is configured to drive the second lifting mechanism to extend or contract, so that the second end moves in a direction away from or close to the housing, thereby adjusting the level degree of the housing.

For example, the support part may include a plurality of second lifting mechanisms. Each second lifting mechanism is correspondingly connected to one third driving element, or two or more second lifting mechanisms are commonly connected to one third driving element, and the third drive element provides different control signals for different second lifting mechanisms, and the plurality of second lifting mechanisms are respectively adjusted for adjusting the level degree of the housing, so that the illumination device is stably supported.

Typically, as illustrated in FIGS. 2 and 3A-3H, the support part 32 includes a second lifting mechanism 33 and a third driving element. The third driving element may include a driving motor 35, a worm gear 36, and a worm 37. One end of the second lifting mechanism 33 away from the housing 1 is provided with a support base 34, and the driving motor 35 drives the worm gear 36 and the worm 37 to operate so that the second lifting mechanism 33 extends or contracts, thereby a distance between the support base 34 and the housing 1 is adjusted. By adjusting the second lifting mechanisms 33 at different positions of the illumination device, the level degree of the illumination device may be adjusted, so that the illumination device has low requirements on flat degree of a terrain where the illumination device is placed.

In this way, during emergency medical treatment, medical personnel may not need to consider how to select an appropriate terrain to place the illumination device. For example, the driving motor 35 may be a 5IK90A-CF type optical axis motor. For example, the second lifting mechanism 33, the support base 34, and the worm 37 may be firmly connected using screws, and the drive motor 35 and the worm gear 36 may be firmly connected using screws.

For example, the worm is at least partially located within the second lifting mechanism, and the inner wall of the second lifting mechanism and the outer wall of the worm are in a threaded connection. Rotating the worm may make the worm screw in and out of the second lifting mechanism. In this way, the driving motor drives the worm gear to rotate, and the worm gear drives the worm to rotate, so that the worm is screwed in and out of the second lifting mechanism, thereby a total length of the worm and the second lifting mechanism is adjusted, i.e. the second lifting mechanism may extend or contract on the housing when viewed from the outside of the housing.

For example, in at least one embodiment of the present disclosure, the second lifting mechanism may be provided as an electric push rod like the first lifting mechanism in the above-described embodiments, and the third driving element may refer to the first driving element in the above-described embodiments. In this way, the third driving element drives the second lifting mechanism to change the length of the second lifting mechanism itself, so that the second lifting mechanism extends or contracts on the housing.

For example, in the illumination device provided by at least one embodiment of the present disclosure, a plurality of the support parts are provided to be served as the supporting foot of the housing, and the control device is configured to adjust the degree of extension and contraction of each second lifting mechanism. In this way, the illumination device may automatically adjust its own level degree without manual operation or with less manual operation.

For example, the illumination device provided by at least one embodiment of the present disclosure further includes a level sensor, which is fixed to the housing and connected to the control device in a signal connection manner. Typically, as illustrated in FIG. 2, a level sensor 38 is installed on the housing 1. The level sensor 38 may monitor the level degree of the illumination device (housing 1) in real time and send corresponding detection information to the control device, and the control device sends an instruction to the support part according to the detection information, so as to adjust the degree of extension and contraction of each second lifting mechanism, thereby the level degree of the illumination device is adjusted. In this way, in a case where the illumination device is placed during the emergency medical treatment, the illumination device may automatically adjust the level degree without human intervention. For example, the level sensor 38 may include an inclination sensor, a gyroscope, or the like. For example, the level sensor 38 may be an A3G4250D gyroscope.

For example, the level sensor may be an electronic gradienter, for example, an inductive gradienter or a capacitive gradienter. For example, the measured level degree may be an inclination angle of a plane of the housing, such as, a bottom surface of the housing relative to a support surface. If the inclination angle is not zero, the plane of the housing, such as, the bottom surface of the housing is not parallel to the support surface, and it is needed to adjust the corresponding second lifting mechanism to make the inclination angle zero.

For example, the level sensor may be a bubble level, and a position of a bubble in the bubble level may be observed to manually control the extension and contraction of the corresponding second lifting mechanism so as to adjust the level degree of the illumination device. For example, if the bubble in the bubble level is on a left side, it is indicated that the left side is higher, thus, the second lifting mechanism on the left side is contracted or the second lifting mechanism on a right side is extended for adjusting.

For example, the second lifting mechanisms may be four, and the bottom surface of the housing may be a quadrangle, such as a rectangle. The four second lifting mechanisms may be respectively arranged at four corners of the quadrangle, or the housing may be circular or oval, etc., and the four second lifting mechanisms may be arranged at equal intervals at edge regions of the housing. Alternatively, the second lifting mechanisms may be five or more, and may be arranged at equal intervals near the edge regions of the bottom surface of the housing.

For example, the illumination device provided by at least one embodiment of the present disclosure further includes an audio controller which is fixed to the housing and is connected to the control device in a signal connection manner. Typically, as illustrated in FIG. 2, the audio controller may include a speaker 10 and a microphone 12 fixed to the housing 1, and the control device 3 includes an audio control chip 11 and a sound signal processing chip 13. The audio control chip 11 is connected to the speaker 10, and the sound signal processing chip 13 is connected to the microphone 12. Through the audio controller, medical personnel may send voice instructions to the illumination device for operation, and the illumination device may also send voice information such as early warning, detection results, operation instructions and the like to the medical personnel according to the detection results, thereby improving functions of the illumination device and simplifying operations of the illumination device. For example, the illumination device may also be provided with a wireless transmission equipment to have a wireless transmission function, so that medical personnel may implement operations such as network inquiry, remote call and the like through the illumination device. For example, the speaker 10 may be an SHD4216 type sounder, the microphone 12 may be an ADMP504ACEZ-RL7 type, the audio control chip 11 may be an 8002B type audio power amplifier chip, and the sound signal processing chip 13 may be a D201-F44 type recording chip.

For example, the illumination device provided by at least one embodiment of the present disclosure further includes a portable belt which is fixed to the housing. Typically, as illustrated in FIGS. 2 and 3A-3H, a portable belt 2 is provided on the housing 1. The portable belt 2 may be hand-held or shoulder-mounted.

For example, in at least one embodiment of the present disclosure, the illumination device may further include a storage battery to store electric power. For example, the control switch 6 illustrated in FIG. 2 may be provided with a switch that controls a power supply function of the storage battery. For example, a storage space may also be provided in the housing of the illumination device, and the storage space may be used for storing medical devices, medicines, etc.

The embodiment of the present disclosure also provides a using method of the illumination device as described above, the using method includes: in a case where a detector is used to detect vital signs of an object to be detected and illumination is required, turning on the illuminator for illumination.

Alternatively, the using method may further include: controlling at least one driving element by using the control device to drive the at least one second lifting mechanism to extend or contract, to adjust a level degree of the housing, so that the illumination device is stably supported.

Alternatively, the using method includes:

detecting a level degree of the housing by adopting the level sensor and transmitting the level degree to the control device;

determining a level degree of the housing according to the level degree detected by the level sensor, and controlling the at least one second lifting mechanism to extend or contract for improving the level degree of the housing in a case where the illumination device is not stably supported.

Alternatively, the using method further includes: inputting a voice signal through a microphone and transmitting the voice signal to a sound signal processing chip, converting the voice signal into a control signal and transmitting the control signal to a control chip by the sound signal processing chip, and controlling the illumination device to perform a corresponding action by the control chip.

Alternatively, in a case where an emergency occurs to the detected object, the control chip controls the audio control chip to initiate the speaker to send out an alarm sound for reminding, or controls the display driving chip to display corresponding reminding information on the display screen.

The embodiment of the present disclosure provides an illumination device and a using method thereof. The illumination device includes a housing, an illuminator and a detector. The illuminator is fixed on the housing, and the detector is installed on the housing and configured to detect vital signs of an object to be detected. The illumination device is provided with a detector to have a vital sign detection function, and users, such as medical personnel, may carry the illumination device to detect the patient condition and monitor in real time the patient condition in the process of performing emergency medical treatment, so that relevant detection equipment may be unnecessary to carry, and the application capability of the illumination device in the medical field is significantly improved.

The following statements should be noted:

(1) The accompanying drawings involve only the structure(s) in connection with the embodiment(s) of the present disclosure, and other structure(s) can be referred to common design(s).

(3) For the purpose of clarity only, in accompanying drawings for illustrating the embodiment(s) of the present disclosure, the thickness and size of a layer or a structure may be enlarged, that is, the accompanying drawings are not drawn according to the actual scale.

(3) In case of no conflict, features in one embodiment or in different embodiments can be combined to obtain a new embodiment.

What are described above is related to the specific embodiments of the disclosure only and not limitative to the scope of the disclosure. The protection scope of the disclosure shall be based on the protection scope of the claims.

The application claims priority to the Chinese patent application No. 201821784783.7, filed Oct. 31, 2018, the disclosure of which is incorporated herein by reference as part of the application.

What is claimed is:

1. An illumination device, comprising:
   a housing;
   an illuminator, fixed to the housing;
   a detector, installed on the housing;
   a control device, fixed to the housing;
   a first lifting mechanism, configured to fix the illuminator to the housing; and
   a first driving element, connected to the control device in a signal connection manner and configured to receive a control signal from the control device to drive the first lifting mechanism to move telescopically for moving the illuminator in a direction away from or close to the housing,
   wherein the detector is configured to detect vital signs of an object to be detected, and
   wherein the control device is connected to the detector in a signal connection manner to receive detection information from the detector.

2. The illumination device according to claim 1, wherein the detector comprises a heart rate sensor, a sphygmomanometer, a temperature sensor or an oximeter, and the detector is magnetically attached to the housing.

3. The illumination device according to claim 2, wherein the housing comprises a first bracket, and a magnet is provided in the first bracket; and
   wherein the detector comprises a casing, and the casing comprises a magnetic material.

4. The illumination device according to claim 1, wherein the illuminator comprises an illumination lamp and a sterilizing lamp.

5. The illumination device according to claim 4, wherein the illuminator further comprises a light converging plate configured to converge light emitted from the illumination lamp and the sterilizing lamp.

6. The illumination device according to claim 1, wherein the control device comprises:
   a control chip, in the housing; and
   a control switch, configured to control power-on and power-off of the control chip.

7. The illumination device according to claim 1, further comprising a display screen, the display screen being fixed to the housing and connected to the control device in a signal connection manner.

8. The illumination device according to claim 1, further comprising:
   a second driving element, connected to the control device in a signal connection manner and configured to drive the illuminator to rotate for adjusting a light emitting angle.

9. The illumination device according to claim 1, wherein the housing comprises a storage tank, and a shape of the storage tank is matched with an outer shape of the illuminator so that the illuminator is accommodated in the storage tank after being retrieved.

10. The illumination device according to claim 1, further comprising:
    a support part, connected to the housing for supporting the illumination device.

11. The illumination device according to claim 10, wherein the support part comprises:
    at least one second lifting mechanism, one end of the second lifting mechanism being connected to the housing and another end of the second lifting mechanism being movable; and
    at least one third driving element, connected to the control device in a signal connection manner and configured to drive the second lifting mechanism to extend or contract so that the other end of the second lifting mechanism moves in a direction away from or close to the housing, thereby adjusting a level degree of the housing.

12. The illumination device according to claim 11, wherein the support part comprises a plurality of second lifting mechanisms, each of the plurality of second lifting mechanism is correspondingly connected to one third driving element, and the plurality of second lifting mechanisms are respectively adjusted for adjusting the level degree of the housing, so that the illumination device is stably supported.

13. The illumination device according to claim 11, wherein the support part comprises a plurality of second lifting mechanisms, at least two of the plurality of second lifting mechanism are correspondingly connected to one third driving element, and the plurality of second lifting mechanisms are respectively adjusted for adjusting the level degree of the housing, so that the illumination device is stably supported.

14. The illumination device according to claim 12, further comprising:
   a level sensor, mounted to the housing and configured to detect the level degree of the housing and transmit the detected level degree to the control device,
   wherein the control device adjusts the plurality of second lifting mechanisms according to the detected level degree.

15. The illumination device according to claim 13, further comprising:
   a level sensor, mounted to the housing and configured to detect the level degree of the housing and transmit the detected level degree to the control device,
   wherein the control device adjusts the plurality of second lifting mechanisms according to the detected level degree.

16. The illumination device according to claim 1, wherein the illumination device is a portable illumination device, and the illumination device further comprises a portable belt provided on an upper side of the housing.

17. The illumination device according to claim 6, wherein the control device comprises:
   an audio control chip, connected to the control chip in a signal connection manner and configured to receive a control instruction from the control chip; and
   a sound signal processing chip, connected to the control chip in a signal connection manner and configured to receive a sound signal and convert the sound signal into a control signal, and transmit the control signal to the control chip.

18. The illumination device according to claim 17, further comprising:
   a speaker, arranged on the housing and connected in a signal connection manner to the audio control chip, and playing a fixed audio signal or an audio signal provided by the audio control chip according to a control of the audio control chip; and
   a microphone, arranged on the housing and configured to receive a sound input from a user and transmit the sound input to the sound signal processing chip.

* * * * *